United States Patent [19]

Casas et al.

[11] Patent Number: 5,837,238
[45] Date of Patent: Nov. 17, 1998

[54] TREATMENT OF DIARRHEA

[75] Inventors: Ivan A. Casas, Raleigh, N.C.; Bo Mollstam, Lerum, Sweden

[73] Assignee: Biogaia Biologics AB, Stockholm, Sweden

[21] Appl. No.: 658,473

[22] Filed: Jun. 5, 1996

[51] Int. Cl.$^6$ .............................. C12N 5/00; A01N 63/00
[52] U.S. Cl. ..................................... 424/93.45; 435/252.9
[58] Field of Search ........................ 424/43.45; 435/252.9

[56] References Cited

PUBLICATIONS

Ling et al. Colonization and Fecal Enzyme Activities after Oral Lactobacillus GG Administration in Elderly Nursing Home Residences, Ann Nutr Metab 36:162–166 (1992).
Publication of Axelsson et al. for "Production of a Broad Spectrum Antimicrobial Substance by *Lactobacillus reuteri*", Microbial Ecol. in Health and Disease 2:131–136 (1989).
Publication of Boudraa et al entitled "Effect of Feeding Yogurt Verss Milk in Children with Persistent Diarrhea", J. Pediatric Gastroenterology and Nutrition 11:509–512 (1990).
Publication of Brunser et al. entitled "Effect of an Acidified Milk on Diarrhoea and the Carrier State in Infants of Low Socio–Economic Stratum", Act Paediatr Scand. 78:259–264 (1989).
Publication of Fabia et al. entitled "The Effect of Exogenous Administration of *Lactobacillus reuteri* R2LC and Oat Fiber on Acetic Acid–Induced Colitis in the Rat", Scand. J. Gastroenterol. 28:155–162 (1993).
Publication of Fuller entitled "Probiotics in Human Medicine", Gut 32:439–442 (1991).
Publication of Goldin et al. entitled "Survival of *Lactobacillus* Species (Strain GG) in Human Gastrointestinal Tract", Digestive Disease and Siences 37:121–128 (1992).
Publication of Isolauri and Vesikari entitled "Oral Rehydration, Rapid Feeding, and Cholestyramine for Treatment of Acute Diarrhea", J. Pediatric Gastroenterology & Nutrition 4:366–374 (1985).
Publication of Isolauri et al. entitled "A Human *Lactobacillus* Strain (*Lactobacillus casei* sp strain GG) Promotes Recovery from Acute Diarrhea in Children", Pediatrics 88:90–97 (1991).
Publication of Isolauri et al. entitled "Diet during *Rotavirus Enteritis* Affects Jejunal Permeability to Macromolecules in Suckling Rats", Pediatric Res. 33:548–553 (1993).
Publication of Isolauri et al. entitled "*Lactobacillus casei* Strain GG Reverses Increased Intestinal Permeability Induced by Cow Milk in Suckling Rats", Gastroenterology 105:1643–1650 (1993).
Publication of Isolauri et al. entitled "Oral Bacteriotherapy for Viral Gastroenteritis", Digestive Diseases and Sciences 39:2595–2600 (1994).

Publication of Isolauri et al. entitled "Improved Immunogenicity of Oral D X RRV Reassortant Rotavirus Vaccine by *Lactobacillus casei* GG", Vaccine 13:310–312 (1995).
Publication of Kaila et al. entitled "Enhancement of the Circulating Antibody Secreting Cell Response in Human Diarrhea by a Human *Lactobacillus* Strain", Pediatric Res. 32:141–144 (1992).
Publication of Kandler et al. entitled "*Lactobacillus reuteri* sp. nov., a New Species of Heterofermentative Lactobacilli", Zbl. Bakt. Hyg., I. Abt. Orig. C 1:264–269 (1980).
Publication of Lidbeck et al. entitled "Impact of *Lactobacillus acidophillus* Supplements on the Human Oropharyngeal and Intestinal Microflora", Scand. J. Infect. Dis. 19:531–537 (1987).
Publication of Majamaa et al. entitled "Lactic Acid Bacteria in the Treatment of Acute Rotavirus Gastroenteritis", J. Pediatric Gastroenterology and Nutrition 20:333–338 (1995).
Publication of Mitsuoka entitled "The Human Gastrointestinal Tract", in: Wood, BJB, Ed. *The Lactic Acid Bacteria Vol. 1. The Lactic Acid Bacteria in Health and Disease*, London: Elsevier Applied Science 1:69–114 (1992).
Publication of Pearce et al. entitled "Controlled Trial of Orally Administered Lactobacilli in Acute Infantile Diarrhea", J. Pediatrics 84:262–262 (1974).
Publication of Perdigon et al. entitled "The Oral Administration of Lactic Acid Bacteria Increase the Mucosal Intestinal Immunity in Response to Enteropathogens", J. Food Protection 53:404–410 (1990).
Publication of Rautanen et al. entitled "Clinical Experience with a Hypotonic Oral Rehydration Solution in Acute Diarrhoea", Acta. Paediatr. 82:52–54 (1993).
Publication of Salminen et al. entitled "Gut Flora in Normal and Disordered States", Chemotherapy 41(Supp):5–15 (1995).
Publication of Tazume et al. entitled "Ecological Study on the Intestinal Bacterial Flora of Patients with Diarrhea", Clinical Infectious Diseases 16(Supp):S77–82 (1993).
Publication of Wolf et al. entitled "Safety and Tolerance of *Lactobacillus reuteri* in Healthy Adult Male Subjects", Microbial Ecology in Health and Disease 8:41–50 (1995).

*Primary Examiner*—Leon B. Lankford, Jr.
*Attorney, Agent, or Firm*—Lynn E. Barber

[57] ABSTRACT

A therapeutic method of treating diarrhea of a patient, such as that caused by rotavirus in which a liquid suspension of one or more strains of *Lactobacillus reuteni* is administered to the patient. Preferably the *L. reuteri* is isolated from an animal of the same species as the animal to which the therapy is being given. Preferably at least about $10^7$ cells of *L. reuteri*, and most preferably, at least $10^8$ cells, are administrated per day, over a period of one to seven days, depending on the severity of the gastroenteritis. The result is a rapid, dramatic reduction in animal's diarrhea and vomiting, previously not found using other therapies.

20 Claims, 4 Drawing Sheets

TREATMENT OF DIARRHEA

BACKGROUND OF THE INVENTION

1. Field of the Invention

This invention relates to therapeutic treatment of infectious gastroenteritis.

2. Description of the Related Art

Normal microflora is important in the protection of the host against diseases of the gastrointestinal (GI) tract (Fuller, R., *Gut* 1991;32:439–42; Salminen, S. et al., *Dig Dis Sci* 1992;10:227–38). During periods of acute diarrhea, the normal gastrointestinal microflora is radically changed. These changes include decreasing numbers of Lactobacilli, Bacteroides and Bifidobacteria (Saiminen S. et al., *Dig Dis Sci* 1992;10:227–38; Tazume S. et al., *Clin Infect Dis* 1993;16(2 suppl):77–82S; Mitsuoka T., in Wood B J B, London:Elsevier Applied Science 1992, 1:69–114; Salminen S. et al., *Chemotherapy*, in press.).

*Lactobacillus reuteri* is the most commonly occurring Lactobacillus species found in the GI tract of humans and animals (Kandler O. et al., *Zbl Bakt Abt Orig* 1980; C1:264–9). Like other Lactobacilli, *L. reuteri* produces acidic metabolic end-products (lactic and acetic acids) which have considerable antimicrobial activity (Axelson L. T. et al., *Microb Ecology Health Dis* 1989;2: 131–6). Use of *L. reuteri* cell therapy for other than probiotic purposes, i.e., benefitting the host by improving the indigenous microflora, or antibiotic purposes, is not known.

Several studies have indicated that the administration of probiotic agents may modulate the microbial balance of the host and attenuate acute periods of diarrhea (Pearce J. L. et al., *J. Pediatr* 1974;84:261–2; Brunser O. et al., *Acta Paediator Scand* 1989;78:259–64; Boudraa G. et al., *J Pediatr Gastroenterol Nutr* 1990; 11:509–12). *Lactobacillus casei* strain GG (LcGG) has been shown to promote clinical recovery from rotavirus gastroenteritis in children and enhance intestinal immune responses (Isolauri E. et al., *Pediatrics* 1991;88:90–7; Kaila M. et al., *Int Pediatr Research Foundation, Inc.* 1992;32:141–4; Majamaa H. et al., *J Pediatr Gastroenterol Nutr* 1995;20:333–8). Other commercially available preparations of lactic acid bacteria, such as, *L. casei* subsp. rhamnosus (Lactophilus), *L. delbruckii* subsp. bulgaricus and others are also being used for the treatment of acute diarrhea, even though their efficacy has not been formally demonstrated (Majamaa H. et al., *J Pediatr Gastroenterol Nutr* 1995;20:333–8). *L. reuteri* has been shown to be safe on exogenous administration to healthy humans (Wolf B. W. et al., *Micro Ecology Health Dis* 1995;8:41–50) and has shown therapeutic potential in a rat model of colitis (Fabia R. et al., *Scand J Gastroenterol* 1993;28:155–62).

*L. reuteri* is known to produce a broad spectrum antimicrobial, called reuterin (Axelson L. T. et al., *Microb Ecology Health Dis* 1989;2: 131–6), which may be responsible for inhibition of pathogenic microorganisms in the gastrointestinal tract.

SUMMARY OF THE INVENTION

The invention herein is a method for treatment of diarrhea utilizing one or more strains of *Lactobacillus reuteri* isolated from an animal of the same species as the animal to which the therapy is being given. Preferably at least about $10^7$ cells of *L. reuteri* are administrated over a period of at least one day, depending on the severity of the gastroenteritis. The result is a rapid, dramatic reduction in the animal's diarrhea and vomiting, previously not found using other therapies.

It is an object of this invention to provide a method of treating acute diarrhea that is more effective and faster in stopping dehydration of young patients than earlier methods.

Other aspects, features and objects of the invention will be more fully apparent from the following disclosure and appended claims.

DETAILED DESCRIPTION OF THE INVENTION AND PREFERRED EMBODIMENTS THEREOF

Figure 1A:
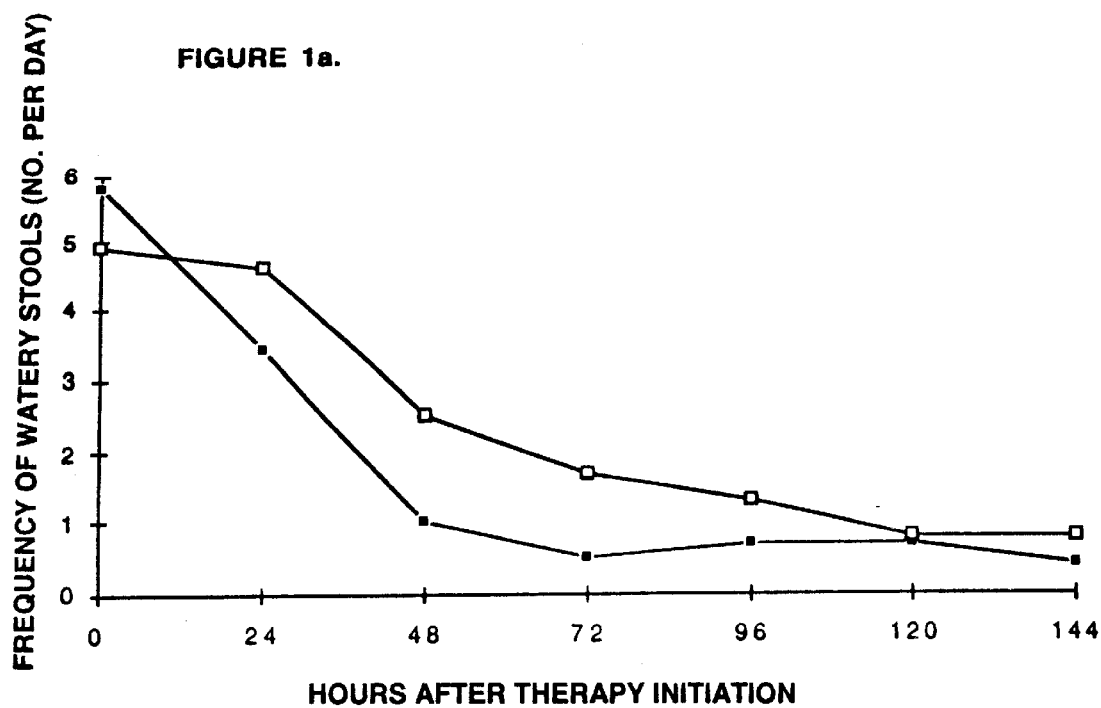
FIG. 1 graphically shows the frequency of watery stools per 24 hour period in patents receiving *L. reuteri* or a placebo, presented as absolute number of diarrheal stools (FIG. 1*a*) and percentage reduction compared to admission level (FIG. 1*b*).

The invention herein is a method of providing therapy to a mammal having diarrhea, comprising determining that the mammal has diarrhea or is imminently susceptible to diarrhea; selecting a strain of *Lactobacillus reuteri*; preparing at least one aliquot of cells of the strain containing about $10^7$–$10^{10}$, preferably at least about $10^8$, cells for administration to the mammal; and orally administering the at least one aliquot to the mammal as soon as possible after diagnosis of diarrhea. The aliquots may be lyophilized cells, which are suspended in a liquid for administration to the mammal. The liquid may be water, fruit juices, dairy products such as milk or yogurt, and the like, which are not harmful to the mammal. The lyophilized cells may be packaged in a moisture impermeable package, such as a foil package, or in a gelatin capsule as is known. As an alternative to liquid administration to the mammal, the lyophilized cells may be placed in a gelatin capsule for administration to the mammal. Preferably the strain of *Lactobacillus reuteri* is one that has been isolated from the same type of mammal to which the therapy is being provided. The invention further comprises a therapeutic preparation for reduction of diarrhea symptoms, comprising at least about $10^7$ viable cells of a strain of *L. reuteri* in an aliquot for administration to a mammal.

The present invention provides a method of treating acute diarrhea in humans, comprising administering *Lactobacillus reuteri*. Preferably, treatments extend over a period of at least one to seven days, preferably begun as soon as possible after diagnosis of diarrhea, with a level of $10^7$–$10^{10}$ cells administered per day. The sooner the treatment begins, the sooner the administered *L. reuteri* cell therapy can eliminate the diarrhea.

In summary of the main study reported herein, to determine the effect of a human Lactobacillus strain (*Lactobacillus reuteri* strain SD 2112) on recovery from acute diarrhea (75% rotavirus), 40 patients between 6 and 36 months of age were studied. This strain of *L. reuteri* has been deposited with the American Type Culture Collection as ATCC No. 55730, under the Budapest Treaty on Dec. 7, 1995, and was originally isolated from human breast milk.

After parental consent, the patients were randomized to one of two groups, and received either $10^{10}$ to $10^{11}$ cfu of *L. reuteri* SD 2112 or a matching placebo daily for the length of hospitalization or up to 5 days. Treatments were administered in 50 to 100 ml of liquid. The mean (SD) duration of watery diarrhea after commencing the therapy in *L. reuteri* group was 1.7 [1.6] days and in placebo group 2.9 [2.3] days (p=0.07). On the second day of treatment only 26% of patients receiving *L. reuteri* had watery diarrhea, as compared with 81% of those receiving the placebo (p=0.0005). Cultures of *lactobacilli* from stool samples demonstrated that administration of *L. reuteri* accounted for more than 75% of the total lactobacilli found in children fed with this product. It is concluded that *L. reuteri* is effective as a therapeutic agent in acute diarrhea in children.

Clinical results, substantiated by faecal analysis, indicate that the colonization of *L. reuteri* in the GI tract resulted in shortening and amelioration of acute diarrhea, mainly of rotavirus etiology. The benefits of *L. reuteri* therapy were observed within 24 hours after treatment started, after which a reduction of watery diarrhea was seen in most patients. The observation that 74% of the treated patients and only 19% of placebo patients were diarrhea free on the second of therapy is clearly of clinical significance. This result compares favorably with the previous experience of Lactobacillus GG (Isolauri E. et al., *Pediatrics* 1991;88:90–7; Majamaa H. et al., *J Pediatr Gastroenterol Nutr* 1995;20:333–8), which in turn was found clinically more effective than a combination *Streptococcus thermophilous* and *L. delbruckii* subsp. Bulgaricus (Yalacta) and *L. casei* subsp. Rhamnosus (Lactophilus) in the treatment of acute diarrhea. The present results may be further improved by earlier administration of *L. reuteri*. In the main study reported herein, *L. reuteri* therapy was started at a relatively late stage of diarrhea in patients requiring hospitalization, and even so only after rehydration and securing of parental consent. In many instances the delay was considerable.

The clinical results were corroborated by the bacteriological findings, which indicated a low total number of lactobacilli and virtual absence of *L. reuteri* in the placebo recipients, and high total lactobacilli and colonization of *L. reuteri* in the treatment group. The colonization data suggests that the presence of *L. reuteri* in the GI tract may improve gut ecology by facilitating the growth of other beneficial microorganisms (Fuller R., *Gut* 1991;32:439–42).

The features and advantages of the present invention will be more clearly understood by reference to the following examples, which are not to be construed as limiting the invention.

EXAMPLES

Patients Studied

The study was carried out between Jan. 29 and Jul. 3, 1995, corresponding to a rotavirus epidemic season. The study protocol had been approved by the Ethical Review Committee of Tampere University Hospital, Tampere, Finland. This was a randomized, double-blind study. Study subjects included 41 well-nourished patients (61% male) between 6 and 36 months of age consecutively admitted to the Department of Paediatrics, Tampere University Hospital, for acute diarrhea of less than 7 days' duration and with more than one watery stool during the previous 24 hours. Children were enrolled in or excluded from the study based on the following inclusion and exclusion criteria. Patients were eligible for study if they were 6 to 36 months of age, admitted for acute diarrhea, had a history of ingesting bovine dairy products (milk, yogurt, infant formula, etc.) as part of their normal diet, and had a parent or legal guardian who signed an informed consent. Patients were excluded from study if they were taking immunosuppressive therapy or suffering from immune deficiency, had a history of allergy to bovine milk, had a serious underlying disease, had taken an investigational product during the preceding month, or had a parent or legal guardian who refused to sign an informed consent.

A randomization schedule was prepared to assign approximately 50% of enrolled patients to each treatment group (*L. reuteri* and placebo). Randomization numbers were sequentially assigned to patients as they were enrolled in the study.

Pre-Study Data Collection

At the time of admission, the children were weighed, clinically examined, and the severity of dehydration was estimated. Acute weight loss was calculated as the difference between expected weight (according to individual growth charts) and observed weight. Fluid deficit (dehydration percent) was then defined from the clinical signs of dehydration and acute weight loss with a reduction of 0.5 to 1% per day of diarrhea had continued for at least 3 days to reflect loss of weight due to low caloric intake. Serum levels of sodium and potassium as well as the blood acid-base balance were determined from a blood specimen collected on admission.

Treatment

After admission to the hospital, the patients were managed according to a standard treatment practice, first with oral rehydration followed by rapid resumption of full feeding (Isolauri E. et al., *J Pediar Gastroenterol Nutr* 1985;4 366–74), but without antidiarrheal drugs. Oral rehydration was accomplished in 6 hours with a solution containing $Na^+$(60 mmol/l) and glucose (84 mmol/l), given at two times the fluid deficit, with a minimum of 30 ml/kg (Rautanen T. et al., *Acta Paediatr* 1993;82:52–4).

Patients were equally randomized to one of two groups. Group 1 (n=19) received $10^{10}$ to $10^{11}$ cfu of *L. reuteri* SD 2112 once a day. Group 2 (n=21) received a matching placebo once a day. The placebo consisted of nonfat dry milk powder. *L. reuteti* and placebo formulations were prepared, quality controlled, and quality assured by BioGaia Biologics, Inc. (Raleigh, N.C., USA) prior to shipping. Each one-gram ($10^{10}$ to $10^{11}$ cfu/g) dose of *L. reuteri* was packaged in freeze-dried form in sterile sealed plastic vials using nonfat dry milk powder as a carrier. One gram freeze-dried preparations of *L. reuteri* or the placebo were reconstituted in 50 to 100 ml of a fluid of choice. Hot food was tempered before mixing with the formulations. The feeding of the assigned preparation was started immediately after the informed consent had been obtained. The patients received *L. reuteri* or placebo for 5 days or for the duration of hospitalization, if shorter.

The patients were weighed daily in the ward. The number and the quality of the stools and vomitus were followed by attending nurses. The stools were recorded as watery, loose or solid. The duration of diarrhea was counted from the last appearance of watery stools. The duration of diarrhea was calculated as decimal days. The patients were discharged according to the clinical judgment of the attending physician. They were asked to contact the investigators if diarrhea recurred in follow-up period of 1 month, at which point they were seen again for the collection of a blood specimen.

Patient Data Collection

Concentrations of serum sodium, potassium, and blood acid-base analysis were determined in the Hospital laboratory using standard procedures.

Rotavirus antigen was demonstrated using a commercial enzyme-immunoassay (Dakopatts AS, Denmark) in the Department of Virology, Medical School, University of Tampere. Blood specimens for rotavirus serology were collected the same day or one day after admission and four weeks later for the determination of rotavirus antibodies. Rotavirus IgA class antibodies were determined using an ELISA method (Isolauri E. et al., *Vaccine* 1995;13:310–2).

Stools were collected from each subject for analysis of total lactobacilli and *L. reuteri*. Fecal samples were collected at baseline prior to study product administration, 48 hours after study product administration and at hospital discharge. No less than 2 g of stools were collected for microbial analysis. The samples were homogenized and diluted in 0.1% peptone water for final ratio of 1:5. Five aliquots of 1.6 ml each of well mixed preparations were quick frozen and stored at −70° C. Diluted stool samples were sent to BioGaia Biologics, Inc., Raleigh, N.C. USA, for the determination of the total faecal lactobacilli and *L. reuteri*.

Faecal activities of the enzymes urease, β-glucuronidase and β-glucosidase were determined in the laboratory of Clinical Nutrition Department of University of Kuopio as previously described (Ling W. H. et al., *Ann Nutr Metab* 1992;36: 162–6).

Statistical Methods

Statistical analysis was performed using Student's t-test and analysis of variance (Anova) to determine statistical differences between study groups. When comparing repeated measurements, the paired t-test and Anova for repeated measures were applied.

Results

Forty-one patients were initially enrolled in the study. One child in the placebo group was removed from the analysis, because *L. reuteri* was found in the stool samples. His sister, also included in the trial, was assigned to the *L. reuteri* group. It was obvious that cross contamination had taken place between these children. Of the remaining 40 children, 19 and 21 patients were assigned to the *L. reuteri* and placebo treatments, respectively. Thirty (75%) patients had rotavirus antigen in the stool specimens by enzyme-immunoassay. Rotavirus was found in the *L. reuteri* group from 12 (63%) patients and in the placebo group from 18 (86%) patients.

The pertinent clinical characteristics of the total study group (n=40) are presented in Table 1:

Clinical Characteristics of Children Hospitalized for Acute Diarrhea and Enrolled in Study

| Clinical Evaluation | Mean ± | SD | Range |
|---|---|---|---|
| Age (months) | 16.5 | 8.8 | 6 to 36 |
| Duration of diarrhea before treatment (days) | 3.0 | 1.7 | 1 to 7 |
| Dehydration (%) | 3.4 | 1.4 | 0 to 7 |
| Acute weight loss (g) | 371 | 188 | 150 to 891 |
| Serum Na$^+$ (mmol/L) | 138 | 3.1 | 130 to 144 |
| Blood | | | |
| pH, actual | 7.35 | 0.06 | 7.24 to 7.46 |
| Base excess (mmol/L) | −7.1 | 4.4 | −15 to +2.3 |

The mean (SD) duration of diarrhea until treatment was 3.0 (1.7) days. On admission most patients had mild dehydration, mean 3.4 (1.4) %. The serum sodium was between 130 and 144 mmol/L, with a mean of 138 mmol/l. The rotavirus-positive patients had diarrhea for 2.6 (1.5) days at home as compared to 3.1 (1.9) days in rotavirus-negative patients (difference not significant). The degree of dehydration in rotavirus-positive children was not significantly more severe than in rotavirus-negative patients, but they had more metabolic acidosis (base deficit 7.8 (4.3) mmol/l) than the non-rotavirus patients on admission (mean base deficit 4.8 (3.8) mmol/l), respectively (p 0.07).

The characteristics of patients receiving *L. reuteri* or placebo are presented in Table 2. On admission, the groups were comparable except that in the *L. reuteri* group the children were more dehydrated than in the placebo group. Weight gain after rehydration was similar in the two groups, as was correction of the metabolic acidosis.

TABLE 2

Clinical Characteristics on Admission of Patients Receiving *L. reuteri* or Placebo

| | *L. reuteri* Group n = 19 | | Placebo Group n = 21 | | |
|---|---|---|---|---|---|
| Clinical Evaluation | Mean ± | SD | Mean ± | SD | P |
| Age (months) | 16.8 | 8.1 | 16.3 | 9.5 | 0.86 |
| Acute weight loss (g) | 415 | 190 | 328 | 181 | 0.15 |
| Dehydration (%) | 3.9 | 1.3 | 3.0 | 1.2 | 0.025 |
| Duration of diarrhea before treatment (days) | 3.1 | 1.7 | 2.8 | 1.8 | 0.66 |
| Blood | | | | | |
| pH, actual | 7.36 | 0.06 | 7.36 | 0.06 | 0.96 |
| Base excess (mmol/L) | −7.6 | 4.4 | −6.6 | 4.4 | 0.50 |
| Serum Na$^+$ (mmol/L) | 138 | 3.1 | 139 | 3.2 | 0.56 |

The clinical outcome of the two treatments was similar for weight gain, correction of acidosis and electrolyte levels (Table 3).

TABLE 3

Clinical Outcome of Patients Receiving *L. reuteri* or Placebo

| | *L. reuteri* Group n = 19 | | Placebo Group n = 21 | | |
|---|---|---|---|---|---|
| Clinical Evaluation | Mean ± | SD | Mean ± | SD | P |
| Weight gain at rehydration | 188 | 270 | 122 | 145 | 0.40 |
| Weight gain at discharge | −4.4 | 293 | −4.7 | 166 | 0.99 |
| Duration of diarrhea in hospital (days) | 1.7 | 1.6 | 2.9 | 2.3 | 0.07 |
| Blood | | | | | |
| pH, after rehydration | 7.38 | 0.04 | 7.39 | 0.03 | 0.49 |
| Base excess (mmol/L) after rehydration | −2.7 | 3.3 | −3.3 | 2.8 | 0.59 |
| Base excess at discharge | −0.6 | 2.5 | −1.6 | 3.4 | 0.44 |
| Serum Na + (mmol/L) | | | | | |
| after rehydration | 139 | 2.0 | 138 | 2.9 | 0.56 |
| at discharge | 139 | 1.9 | 139 | 3.0 | 0.63 |

The duration of watery diarrhea was shorter in the *L. reuteri* (p=0.07). Days 0, 1, 2, 3, 4, 5 and 6 were calculated as 24 hour periods before or after administration of *L. reuteri* or placebo. The effect of *L. reuteri* on persistence of water diarrhea is further presented in Table 4 and FIGS. 1a and 1b.

TABLE 4

Percent of Patients with Watery Diarrhea

| Days of Therapy[1] | All Patients n = 40 Ratio[2] (%) | L. reuteri Gp. n = 19 Ratio[2] (%) | Placebo Gp. n = 21 Ratio[2] (%) | p[3] |
|---|---|---|---|---|
| Day-0 | 40/40 (100) | 19/19 (100) | 21/21 (100) | |
| Day-1 | 37/40 (93) | 16/19 (84) | 21/21 (100) | 0.06 |
| Day-2 | 22/40 (55) | 5/19 (26) | 17/21 (81) | 0.0005 |
| Day-3 | 13/40 (33) | 2/19 (11) | 11/21 (53) | 0.004 |
| Day-4 | 9/40 (23) | 3/19 (16) | 6/21 (24) | 0.33 |
| Day-5 | 5/40 (13) | 2/19 (11) | 3/21 (14) | 0.71 |
| Day-6 | 5/40 (13) | 2/19 (11) | 3/21 (14) | 0.71 |

[1]Day 0, 1, 2, 3, 4, 5 and 6 correspond to 24 h prior to administration and 24, 48, 72, 96, 120, and 144 h post administration, respectively.
[2]With diarrhea/total.
[3]Comparison of L. reuteri and Placebo groups.

Figure 1B:
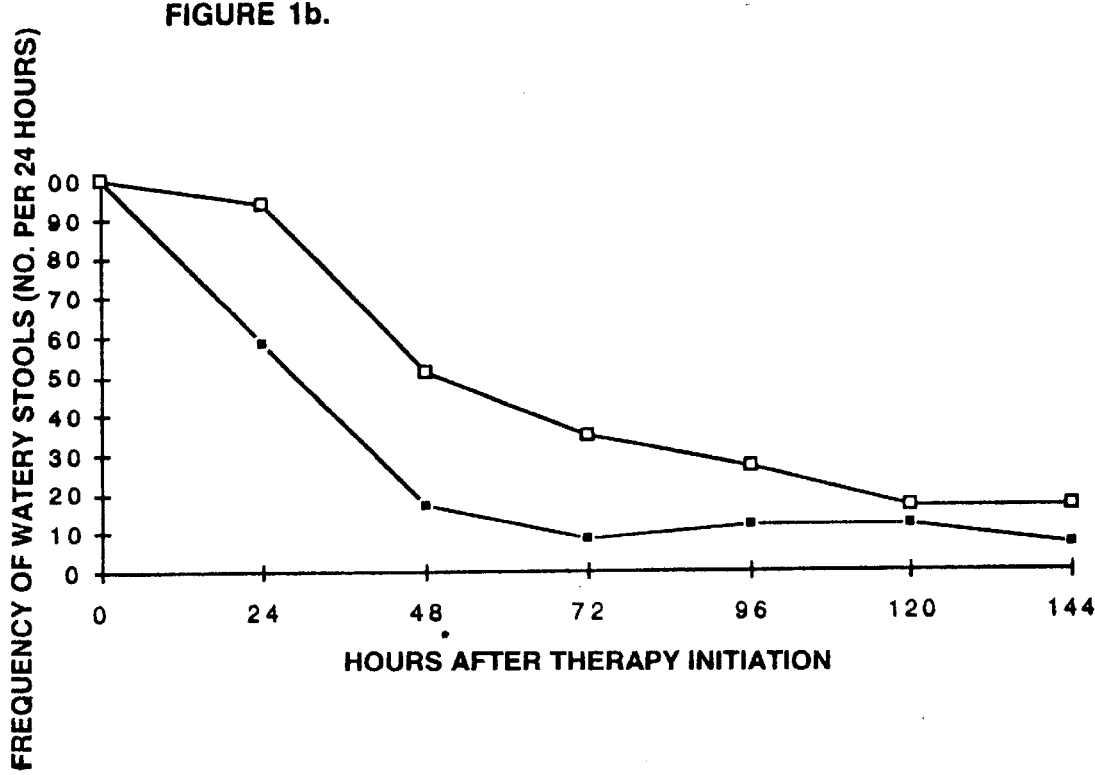

By the second day of treatment watery diarrhea persisted in only 26% of L. reuteri recipients and as compared with 81% of placebo recipients. On the second day the frequency of watery stools decreased in the L. reuteri group; the means were 1.0 (SD 2.3) in the L. reuteri group and 2.5 (SD 2.3) in the placebo group (p=0.05) (FIG. 1a). On the third day the mean frequency of watery stools was 0.5 (SD 1.9) in the L. reuteri group and 1.7 (SD 2.6) in the placebo group (p=0.12).

Fewer patients receiving L. reuteri, compared with those receiving placebo, had vomiting, starting from the second day of treatment (Table 5).

TABLE 5

Percent of Patients with Vomiting

| Days of Therapy[1] | All Patients n = 40 Ratio[2](%) | L. reuteri Gp. n = 19 Ratio[2](%) | Placebo Gp. n = 21 Ratio[2](%) | p[3] |
|---|---|---|---|---|
| Day-0 | 23/40(58) | 7/19(37) | 16/21(76) | 0.01 |
| Day-1 | 12/40(30) | 6/19(32) | 16/21(29) | 0.83 |
| Day-2 | 4/40(10) | 0/19(0) | 4/21(19) | 0.04 |
| Day-3 | 6/40(15) | 1/19(5) | 5/21(24) | 0.18 |
| Day-4 | 4/40(10) | 0/19(0) | 4/21(19) | 0.04 |
| Day-5 | 2/40(5) | 0.19(0) | 2/21(10) | 0.16 |
| Day-6 | 2/40(5) | 0/19(0) | 2/21(10) | 0.16 |

[1]Day 0, 1, 2, 3, 4, 5 and 6 correspond to 24 h prior to administration and 24, 48, 72, 96, 120, and 144 h post administration, repectively.
[2]Vomiting/total.
[3]X[2]test (chi square test).

Figure 2A:
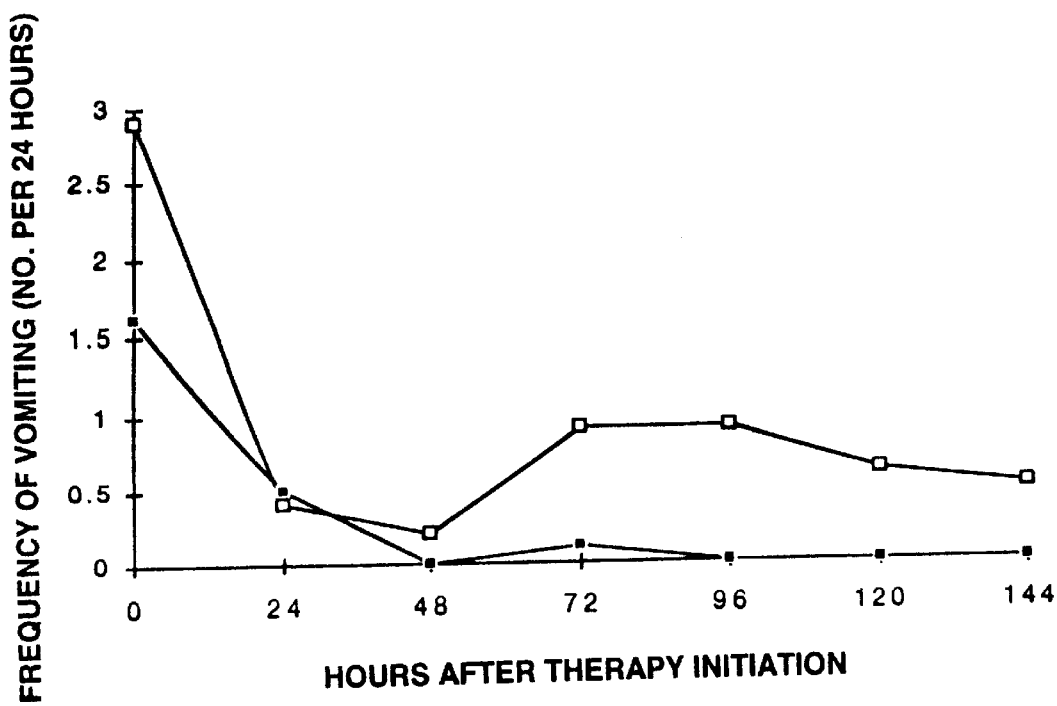
FIG. 2 shows the frequency of vomiting per 24 hour period in patients receiving *L. reuteri* or a placebo, presented as absolute number of vomiting episodes (FIG. 2*a*) and percent reduction from the admission level (FIG. 2*b*).
Figure 2B:
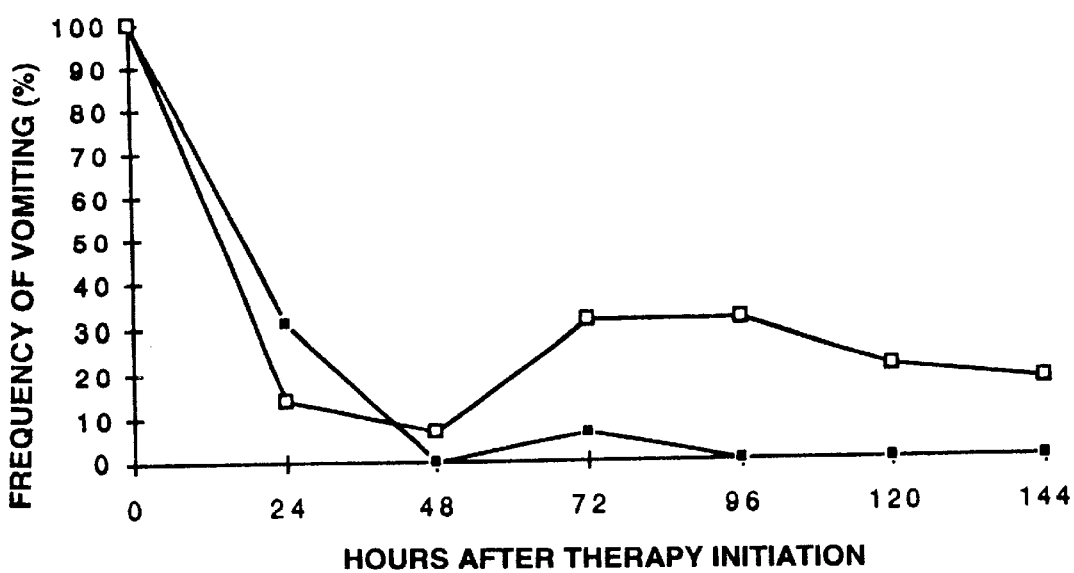

FIGS. 2a and 2b also illustrate the vomiting results. Vomiting practically stopped after the first day of therapy in the L. reuteri group, while in the placebo group it still lingered until the sixth day.

Figure 3:
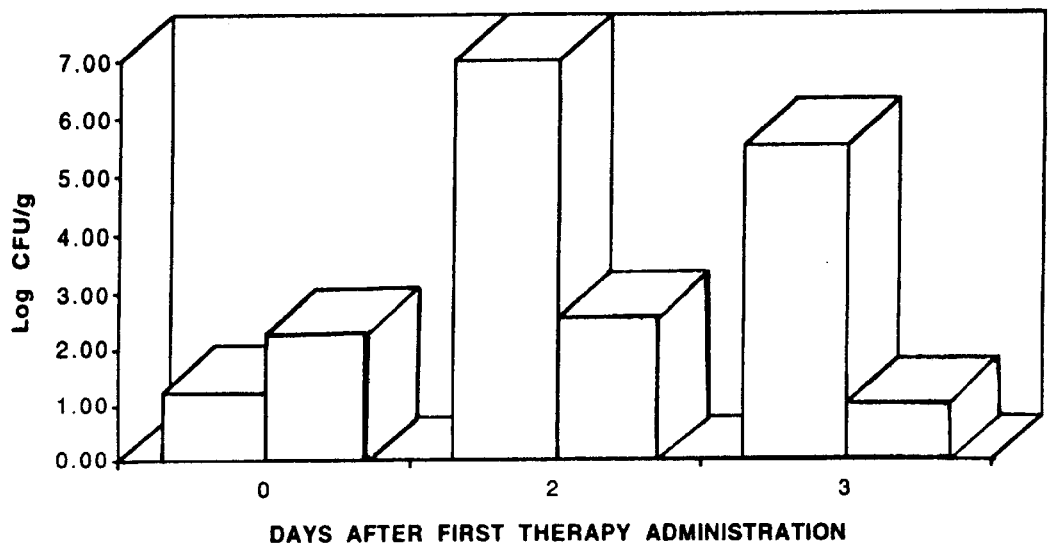
FIG. 3 shows the total fecal lactobacillus in the placebo and in *L. reuteri*—fed children.
Figure 4:
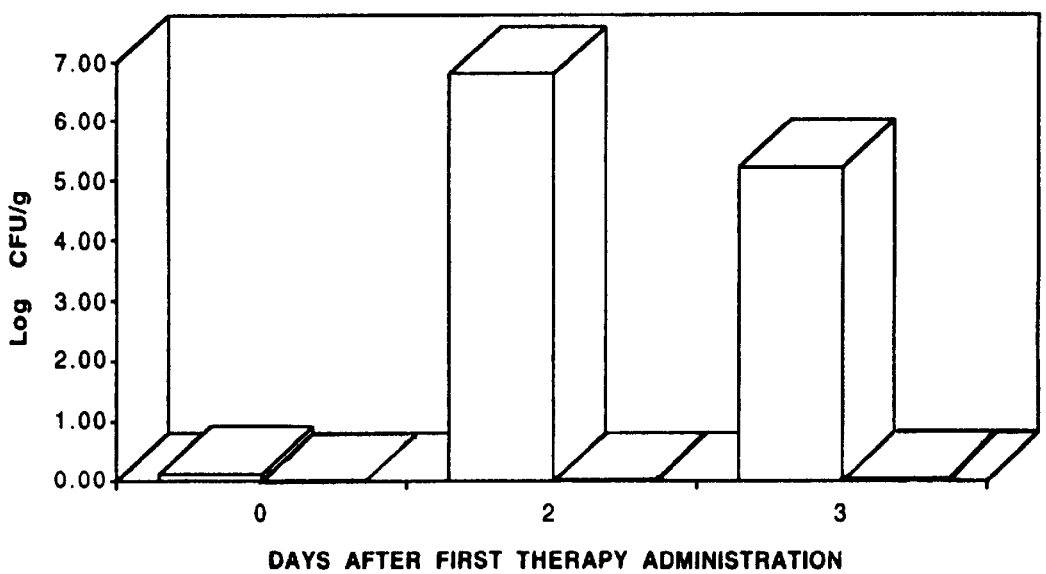
FIG. 4 shows the fecal *L. reuteri* count in the placebo and in *L. reuteri*—fed children.
Figure 5:
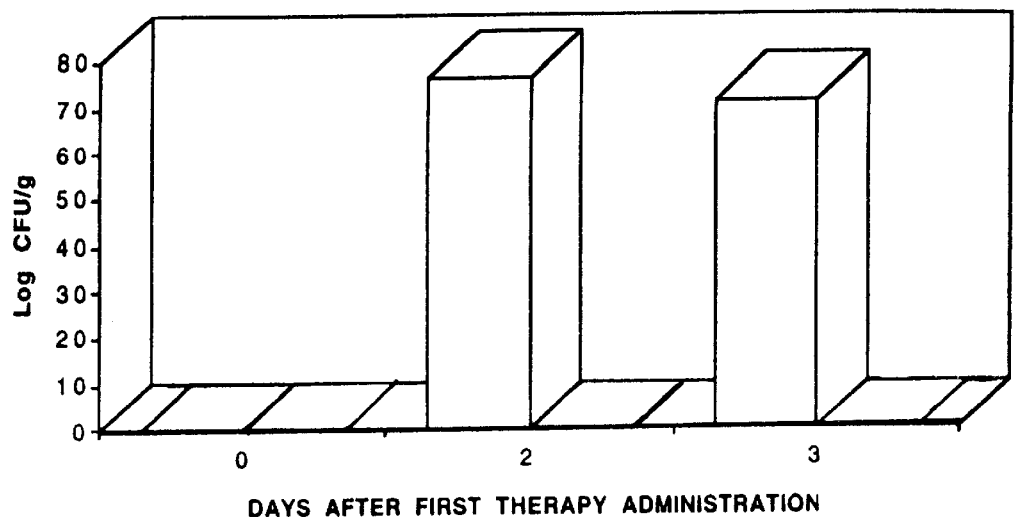
FIG. 5 shows the *L. reuteri* as a percent of the total fecal Lactobacillus population in the placebo and in *L. reuteri*—fed children.

Administration of L. reuteri resulted in good colonization of the gastrointestinal tract (FIGS. 3–5 and Table 6).

TABLE 6

Faecal total lactobacilli and L. reuteri in patients treated with L. reuteri or placebo.

| Clinical Evaluation | L. reuteri Group n = 19 mean | SD | Placebo Group n = 21 mean | SD | P[1] |
|---|---|---|---|---|---|
| Total Lactobac. (log CFU/g) | | | | | |
| Base line stool samples | 2.71 | 1.57 | 3.08 | 1.69 | 0.41 |
| 48 hr stool | 6.88 | 1.54 | 3.32 | 1.99 | 0.0001 |
| Discharge stool | 5.78 | 2.31 | 2.48 | 1.26 | 0.0025 |
| L. reuteri (log CFU/g) | | | | | |
| Base line stool samples | 1.86 | 0.06 | 1.85 | 0.00 | 0.29 |
| 48 hr stool | 6.70 | 1.48 | 1.85 | 0.00 | 0.001 |
| Discharge stool | 5.45 | 2.57 | 1.85 | 0.00 | 0.008 |
| L. reuteri (% Lactobac.) | | | | | |
| Base line stool samples | 0.02 | 0.04 | 0.001 | 0.00 | 0.29 |
| 48 hr stool | 78.7 | 33.9 | 0.01 | 0.00 | 0.0001 |
| Discharge stool 1 | 71.5 | 48.6 | 0.01 | 0.00 | 0.0005 |

[1]Student's t-test (p < 0.05-statistically significant difference)

As shown, a net increment of $10^7$ CFU/g of L. reuteri in feces was observed after 48 hours of L. reuteri administration. Total lactobacilli CFUs also showed an increment of $10^5$ CFU/g in feces 48 hours after the initial dose of L. reuteri (Table 6). L. reuteri accounted for more than 75% of total lactobacilli detected in stool samples. Total lactobacilli were low in the stools of placebo treated children, and L. reuteri was not detected in any of those stool samples. Throughout the study total faecal lactobacilli from placebo treated children were in the range of $10^1$ to $10^5$ CFU/g.

Fecal activities of the bacterial enzymes urease, β-glucuronidase (β-GLN), and β-glucosidase (β-GLS) were lower in the L. reuteri group than in the placebo group (Table 7).

TABLE 7

Fecal enzyme activities: β-GLN, β-GLS, and urease in L. reuteri and placebo groups (mmol × min$^{-1}$ × mg protein$^{-1}$)

| | L. reuteri group n = 12 median | IQR range | Placebo group n = 9 median | IQR[2] range | P[1] |
|---|---|---|---|---|---|
| β-GLN-0 | 0.10 | 0–0.37 | 0.26 | 0.037–0.67 | 0.28 |
| β-GLN-2 | 0.27 | 0–0.1 | 0.17 | 0–1.16 | 0.54 |
| β-GLN-3 | 0.11 | 0–0.22 2 patients | 0.29 | 0.01–1.27 5 patients | 0.33 |
| β-GLS-0 | 0.47 | 0–1.29 | 0.39 | 0–2.32 | 0.72 |
| β-GLS-2 | 0.97 | 0–4.55 | 1.82 | 0.44–2.79 | 0.99 |
| β-GLS-3 | 0.52 | 0–1.04 2 patients | 0.67 | 0.03–2.42 5 patients | 0.56 |
| Urease-0 | 0 | 0–2.09 | 1.23 | 0–23.66 | 0.22 |
| Urease-2 | 0.96 | 0–6.05 | 4.25 | 0–7.72 | 0.64 |
| Urease-3 | 0 | 0 2 patients | 12.12 | 1.90–18.62 5 patients | 0.12 |

[1]non parametric test (Mann-Whitney U)
[2]within a 95% confidence level

Rotavirus IgA class (circulating) antibodies were similar in the two study groups. On admission, the mean rotavirus IgA antibody levels in the L. reuteri group was 22.5 (SD 39.8) enzyme immunounits (EIU) and in the placebo group 7.99 (SD 21.8) EIUs (p=0.163). Four weeks later the mean rotavirus IgA antibody levels were 74.2 (SD 33.9) and 66.3 (SD 31.9) (p=0.4705) in the *L. reuteri* and in the placebo groups, respectively, indicating that diarrhea symptoms were decreased without need for an apparent increase in IgA levels, unlike results seen with Lactobacillus GG.

Early Administration

Administration of *L. reuteri* according to the invention is best as soon as there are diarrhea symptoms. Thus, when the treatment according to the invention as discussed above is administered on the first day when diarrhea symptoms are present, there is a substantial reduction in watery diarrhea and vomiting as compared to controls. This difference is most marked in rotavirus gastroenteritis.

Low Dosage Levels

Patients are given varying levels of *L. reuteri* from $10^7$ to $10^{10}$ per day, which treatments provide similar decreases in diarrhea symptoms, with the rapidity of recovery being increased at the higher levels.

Form of Treatment with *L. reuteri*

In addition to use of a liquid suspension of *L. reuteli*, either freshly grown or as lyophilized cells resuspended in a chosen liquid, patients are given the same number of *L. reuteri* cells in a gelatin capsule, once a day. Particularly for mammals which already receive a pastelike nutritional supplement, the *L. reuteri* therapy may be included in the paste given to the mammal on at least a daily basis when diarrhea symptoms are noticed or when the mammal is likely to be susceptible to diarrhea (e.g., weaning). The same results, reduced diarrhea symptoms, are observed with each of these types of formulation.

Multiple Daily Administration

In cases where the diarrhea symptoms are particularly severe at the beginning of therapy with the invention, administration of multiple aliquots of *L. reuteri* remedies the problem of the therapy being excreted from the body before having a chance to have its effect. Such instances include severe infant or child diarrhea.

Treatment of Other Mammals

The same diminution of diarrhea symptoms are observed in other mammalian systems with the therapy of the invention. Thus, administration of about $10^7$–$10^{10}$ cells per day to piglets prior to and/or at weaning reduces the incidence of rotavirus-induced diarrhea in pigs.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of treating acute diarrhea that is efficient and rapid in stopping dehydration of young patients, comprising:
   a) determining that the patient has diarrhea or is imminently susceptible to diarrhea;
   b) selecting a strain of *Lactobacillus reuteri;*
   c) preparing at least one aliquot of cells of the strain containing about $10^7$–$10^{10}$ cells for administration to the patient; and
   d) orally administering the at least one aliquot to the patient as soon as possible after diagnosis of diarrhea.

2. The method of claim 1, wherein preparing the at least one aliquot comprises lyophilizing the cells, and further comprises a step selected from the group consisting of suspending the lyophilized cells in liquid, enclosing the lyophilized cells in a gelatin capsule, and enclosing the lyophilized cells in a moisture-impermeable container for storage until administered to the patient.

3. A method of providing therapy to a mammal having diarrhea, comprising:
   a) determining that the mammal has diarrhea or is imminently susceptible to diarrhea;
   b) selecting a strain of *Lactobacillus reuteri;*
   c) preparing at least one aliquot of cells of the strain containing about $10^7$–$10^{10}$ cells for administration to the mammal; and
   d) orally administering the at least one aliquot to the mammal as soon as possible after diagnosis of diarrhea.

4. The method of claim 3, wherein about at least $10^8$ cells are administered to the mammal once per day until the mammal is diarrhea-free.

5. The method of claim 3, wherein preparing said at least one aliquot comprises lyophilizing the cells.

6. The method of claim 5, wherein the lyophilized cells are suspended in a liquid prior to administration.

7. The method of claim 6, wherein the liquid is selected from the group consisting of juices, dairy products and water.

8. The method of claim 5, further comprising enclosing the lyophilized cells in a gelatin capsule for administration to the mammal.

9. The method of claim 5, further comprising enclosing the lyophilized cells in a moisture-impermeable container for storage until administered to the mammal.

10. The method of claim 3, wherein the diarrhea is associated with rotavirus infection.

11. The method of claim 3, wherein the mammal is a human.

12. The method of claim 3, wherein the strain was isolated from the same type of mammal as the mammal to which the therapy is being provided.

13. The method of claim 12, wherein the strain was isolated from a human.

14. The method of claim 13, wherein the strain was isolated from human breast milk.

15. A therapeutic preparation for reduction of diarrhea symptoms, comprising at least about $10^7$ viable cells of a strain of *Lactobacillus reuteri* in an aliquot for administration to a mammal.

16. The therapeutic preparation of claim 15, wherein the cells are lyophilized and packaged in a moisture-impermeable container.

17. The therapeutic preparation of claim 15, wherein the cells are suspended in a liquid.

18. The therapeutic preparation of claim 17, wherein the liquid is selected from the group consisting of water, dairy products, and fruit juices.

19. The therapeutic preparation of claim 15, wherein the cells are lyophilized and placed in a gelatin capsule for administration to the mammal.

20. The therapeutic preparation of claim 15, wherein the strain was isolated from a human, and the preparation is for human use.

* * * * *